United States Patent [19]

Hollmann et al.

[11] Patent Number: 4,541,442
[45] Date of Patent: Sep. 17, 1985

[54] HEAT TREATMENT APPARATUS FOR HEATING HUMAN HAIR ON THE HEAD

[75] Inventors: Siegfried Hollmann, Darmstadt; Dieter Hoch, Pfungstadt; Heribert Bollinger, Worms, all of Fed. Rep. of Germany

[73] Assignee: Wella Aktiengesellschaft, Darmstadt, Fed. Rep. of Germany

[21] Appl. No.: 463,861
[22] PCT Filed: Aug. 16, 1982
[86] PCT No.: PCT/EP82/00173
§ 371 Date: Jan. 20, 1983
§ 102(e) Date: Jan. 20, 1983
[87] PCT Pub. No.: WO83/00606
PCT Pub. Date: Mar. 3, 1983

[30] Foreign Application Priority Data

Aug. 27, 1981 [DE] Fed. Rep. of Germany ....... 3133851

[51] Int. Cl.⁴ ............................................. A45D 1/00
[52] U.S. Cl. ............................................. 132/9; 34/39; 219/499
[58] Field of Search ............. 132/9, 7, 33 R; 34/39, 34/99; 219/354, 553

[56] References Cited

U.S. PATENT DOCUMENTS

| 2,281,184 | 4/1942 | Dykstra et al. ............. 34/39 |
| 2,574,621 | 11/1951 | Chun ........................ 34/39 |
| 3,289,679 | 12/1966 | Zellerman ................... 132/9 |
| 3,464,425 | 9/1969 | Gagliano .................... 132/9 |
| 4,224,955 | 9/1980 | Meyerhoefer ............. 132/33 R |
| 4,256,127 | 3/1981 | Tsujimoto ................... 34/98 |
| 4,257,172 | 3/1981 | Townsend ................... 34/39 |
| 4,259,566 | 3/1981 | Kobayashi ................... 132/9 |
| 4,265,029 | 5/1981 | Jenkins .................... 34/39 |

FOREIGN PATENT DOCUMENTS

| 7810814 | 4/1978 | Fed. Rep. of Germany . |
| 944623 | 4/1949 | France . |
| 7518037 | 1/1977 | France . |
| 604606 | 9/1978 | Switzerland . |
| 611663 | 5/1946 | United Kingdom . |
| 617081 | 3/1947 | United Kingdom . |

Primary Examiner—Gregory E. McNeill
Attorney, Agent, or Firm—Michael J. Striker

[57] ABSTRACT

The heat treatment apparatus comprises at least three, preferably four, infra-red radiators with arcuate linear heating elements. Two radiators are arranged laterally and one, preferably two, central radiators are arranged above the human head. A support arm is displaceably mounted on a ground stand or a wall bracket. The radial median axes (26) of the lateral radiators (6) include between them an angle ($\beta$) of at least 80°, preferably 108°. The ratio between the length of each linear heating element of the radiator, preferably comprising a quartz glass tube, and its radius of curvature (R) amounts to at least 0.2, preferably 0.6. Preferably, the radial median axes of the two central radiators include between them an angle ($\gamma$) of at least 45°, preferably approximately 68.5°, the lower central radiator (9) preferably being swingable downwardly through preferably 30° for the treatment of hair of shoulder length. Owing to the arrangement and construction of the infra-red radiators as well as the use of an optical location device for the head, a uniform temperature distribution on the hair as well as facilitation of operation can be attained.

23 Claims, 11 Drawing Figures

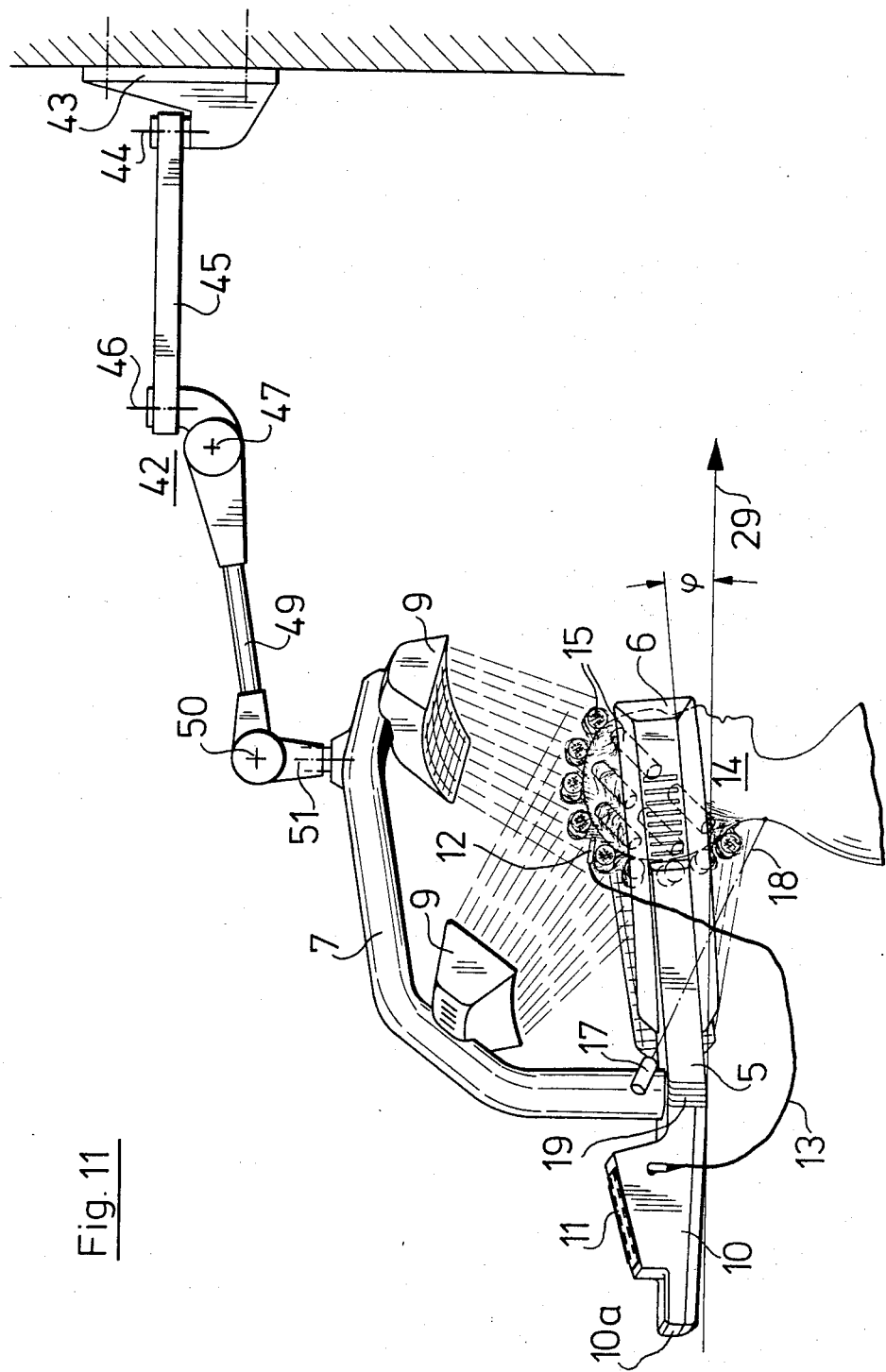

HEAT TREATMENT APPARATUS FOR HEATING HUMAN HAIR ON THE HEAD

BACKGROUND OF THE INVENTION

This invention relates to heat treatment apparatus for heating human hair on the head by means of a plurality of infra-red radiators fastened to a support.

Various forms of heat treatment apparatus are already known, for example that described in French Patent Specification No. 944 623, in which a respective infra-red lamp is attached to each of three mutually displaceable arms of a ground-supported stand. Apparatus having freely displaceable open radiator lamps lack uniform irradiation of the entire head surface. The considerable disadvantage results in that positional adjustment must be performed individually for each lamp in order to avoid local overheating of the hair. Further known heat treatment apparatus, such as that described in French Patent Specification No. 922 103, having a rigid arrangement of the infra-red radiators and a closed reflector casing, irradiates the hair with too low a total heating power, so that a long dwelling time becomes necessary.

SUMMARY OF THE INVENTION

It is an object of the invention to construct a heat treatment apparatus of the kind referred to above, in particular for permanent waving treatment, remedial treatment, or drying treatment in a hairdressing saloon, in such a manner that its operation is simplified and the risk of local overheating is reduced.

The present invention provides heat treatment apparatus in which at least three infra-red radiators constructed as surface radiators with a substantially line-shaped heater body curved like a circle segment are securely attached to the support arm which is displaceably mounted on a ground supported stand or a wall bracket, the infra-red radiator consisting of two lateral infra-red radiators and a central infra-red radiator which, in the position of use, is disposed thereabove, the centre axes, each of which extends in the direction of a radius of curvature, of two laterally disposed infra-red radiators include between them an angle of at least 80°, and the ratio of the length of the curved line-shaped heater body to the radius of curvature thereof amounts to at least 0.2.

An advantage of the open manner of construction is that operations on the hair can be performed during the irradiation process. It is advantageous above all during the drying of permanently waved hair. It is convenient for a temperature sensor to be arranged in the hair, preferably on the surface of a curl roller wound over with a strand of hair, which temperature sensor adjusts the heating power of the infra-red radiators to a predetermined nominal temperature by means of a control module which is preferably located in a control desk.

For the heat treatment, quite particularly for the very sensitive permanent waving treatment of the hair, the technical result depends in relatively narrow limits upon the heat energy and the dwell period. The heat energy parameter can be metered extremely accurately by means of the temperature regulation controlled by the temperature sensor. An advantage of the heat treatment apparatus according to the invention is the extremely uniform irradiation of all hair sections (neck, upper head, sides) with a high radiation energy.

In order to process chemical preparations in a faster and optimum manner, an accurately metered heat supply is of great usefulness. When these preparations operate without additional supply of heat, solely the momentary room temperature is present as energy supplier. Since this room temperature fluctuates strongly (dependent upon summer, winter, time of day), an exact statement of the process times is impossible. By means of a heat treatment apparatus a defined hair temperature is to be adjusted which lies above the room temperature. In order to obtain a uniform reaction of the chemical preparation, the temperature must be maintained constant as far as possible at each location of the hair.

Starting from the chemical consistency of the products, it has furthermore been investigated which kind of heat transmission is best suited. Since the products contain a very high percentage of water, a radiation heat source is preferably selected which has its radiation maximum in the region in which the highest absorption maximum of water is located. It is found that the optimum region lies in the range 2.3 $\mu$m to 2.7 $\mu$m, preferably 2.5 $\mu$m. These results agree unambiguously with the theory of absorption by thin water layers.

Further preferred features of the invention are specified in the sub-claims.

The invention will be described further, by way of example, with reference to the accompanying drawings, which are partly diagrammatically simplified and illustrate two embodiments of heat treatment apparatus. In the drawings mutually corresponding parts are provided with the same reference numerals, and all details not necessary for understanding the invention have been omitted.

BRIEF DESCRIPTION OF DRAWINGS

FIG. 11 is a side view of a second embodiment in the first position of use similar to FIG. 1, but constructed as a wall-mounted apparatus.

DETAILED DESCRIPTION OF THE PREFERRED EMBODIMENTS

Figure 1:
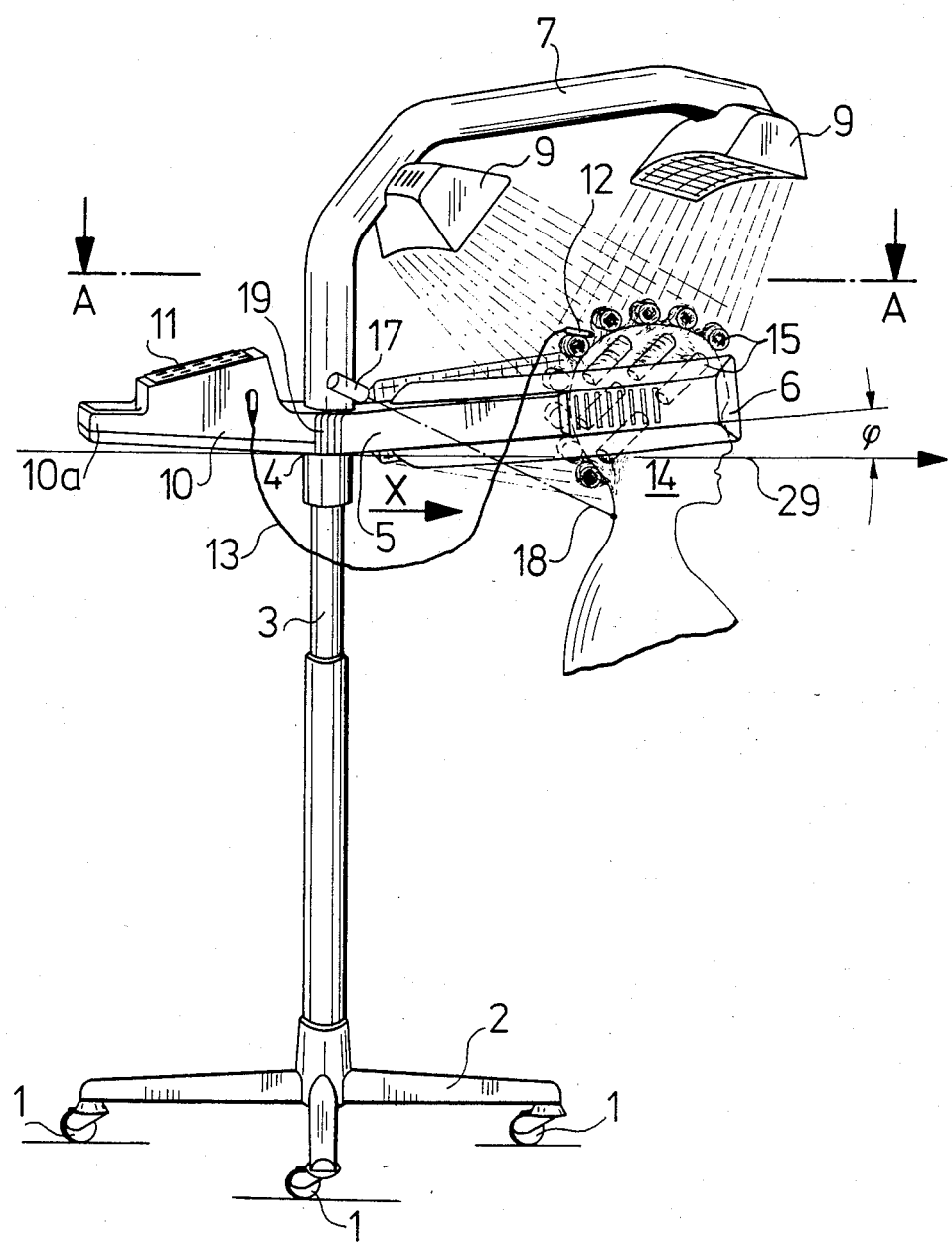
FIG. 1 is a side view of a ground-supported apparatus in a first position of use with lateral infra-red radiators swung to an upper tilt position (in conjunction with a head to be treated)
Figure 2:
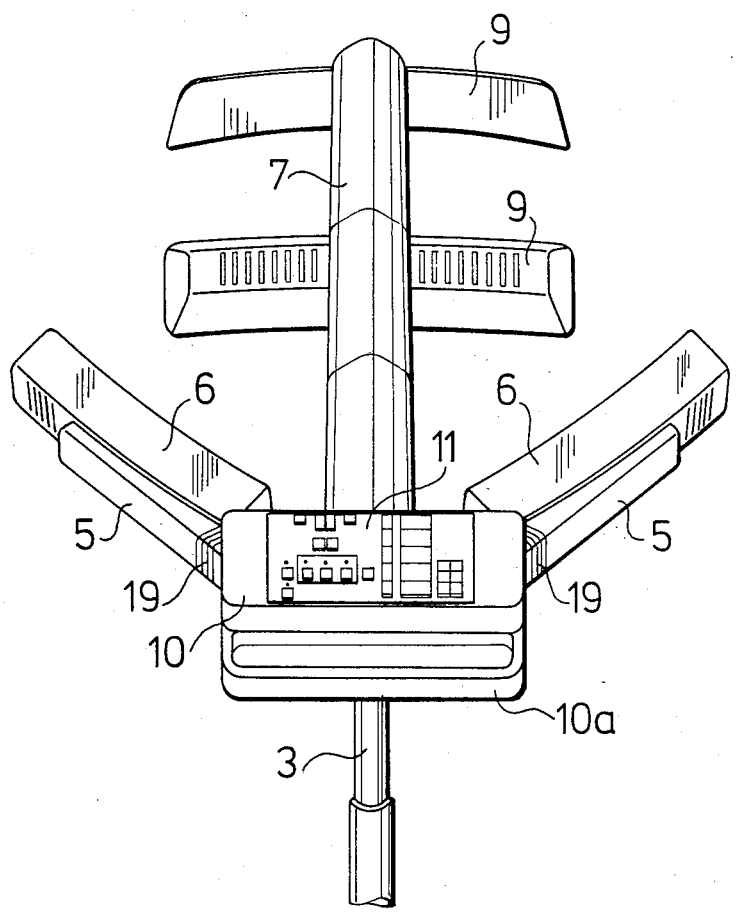
FIG. 2 is a rear view in the direction of the arrow X in FIG. 1, likewise in the first position of use.
Figure 3:
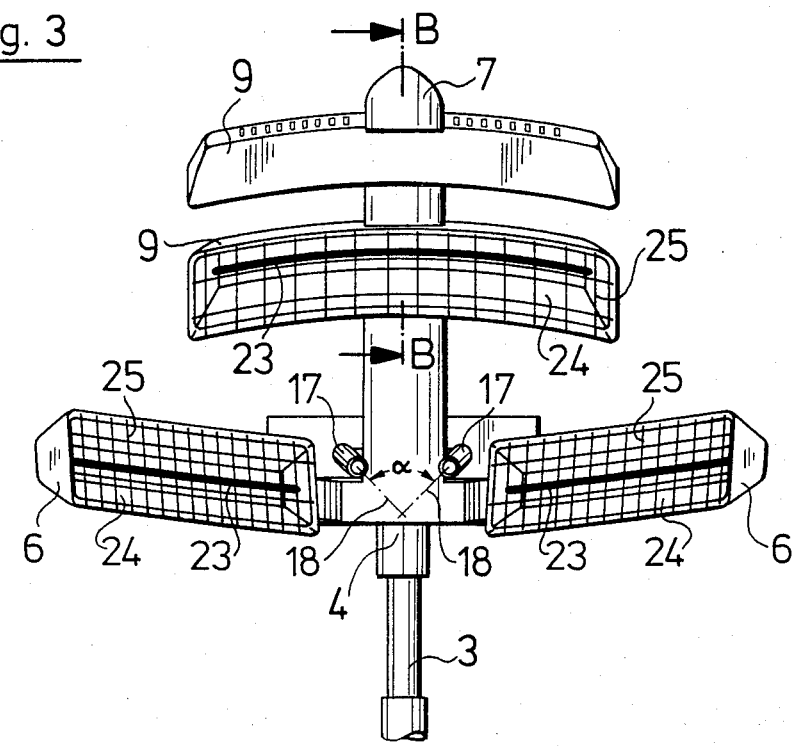
FIG. 3 is a front view of the apparatus shown in FIG. 1, again in the first position of use.

The heat treatment apparatus illustrated in FIGS. 1 to 3 has a stand comprising a cruciform base 2 running on casters 1 and supporting a vertical tube 3 which is selectively longitudinally displaceable and axially rotatable. Two side arms 5 at the upper end 4 of the stand tube 3 each carry a lateral infra-red radiator 6. Furthermore, the upper end 4 carries a substantially horizontally projecting support arm 7 to which two substantially downwardly radiating central infra-red radiators 9 are secured. The upper end 4 of the stand tube 3 is provided with a control desk 10 with a control panel 11 on the side remote from the infra-red radiators 6,9. A handgrip 10a fastened to the desk 10 permits common vertical adjustment and rotation of the infra-red radiators 6,9.

The control desk 10 is connected to a temperature sensor 12 by a flexible lead 13. FIG. 1 shows a human head 14 with hair wound on curl rollers 15 in the radiation region of the radiators 6,9, from which the treatment arrangement may be seen. One of the rollers 15 holds the temperature sensor 12 in contact with the strand of hair wound on it by means of a clip (not shown).

Figure 9:
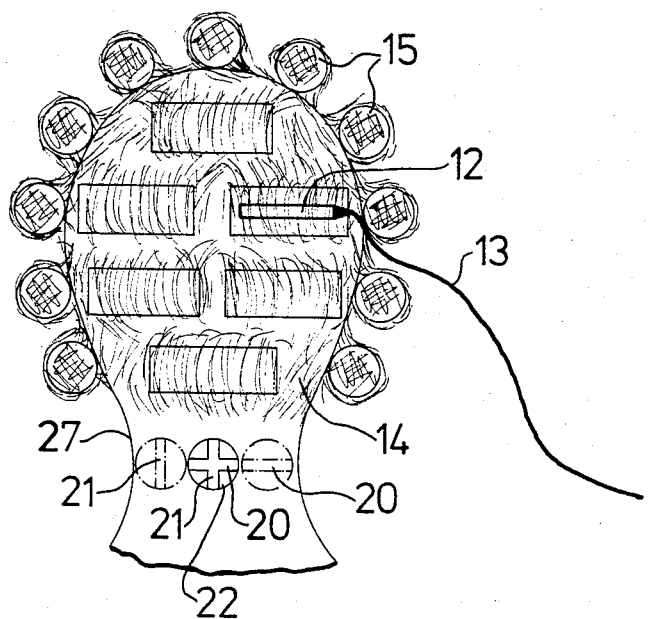
FIG. 9 is a rear view of the head to be treated, with wound curl rollers, showing the cross produced on the head by means of an optical adjustment device, for the correct as well as for the wrong spacing of the head.

For the purpose of adjusting the optimum head spacing between radiators 6,9 and the head 14, the upper end 4 of the stand tube 3 carries an optical adjusting device for fixing the position of the head 14; it is formed by two adjacently disposed projector lamps 17 providing two intersecting optical beams whose axes 18 together form an angle, $\alpha$, preferably of 24° to 35°. The lamps 17 produce on the head 14 in the region of the hair line (neck contour 27) a bright horizontal line 20 and a vertical line 21, respectively, which with a correctly adjusted head spacing are each reproduced sharp and preferably form a cross 22 with equal limbs, as illustrated in FIG. 9. If the head spacing is wrong, the two lines 20 and 21 are located side by side, as additionally illustrated in dot-dash lines in FIG. 9.

Figure 4:
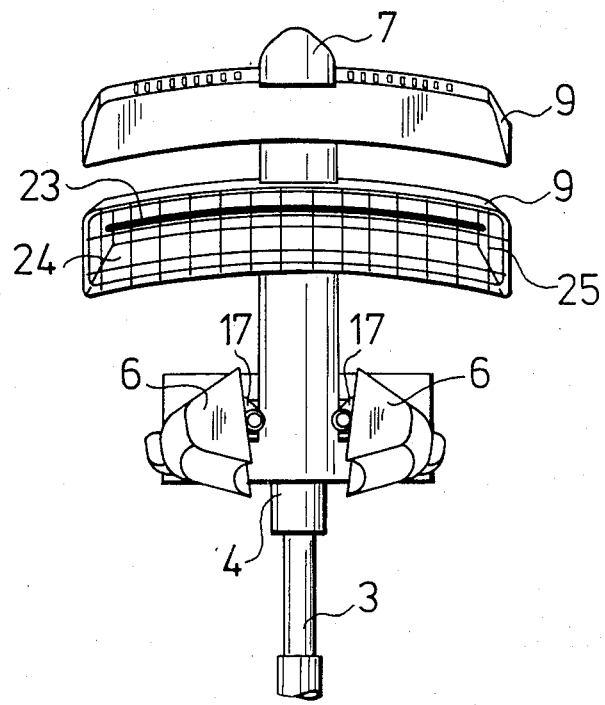
FIG. 4 is a front view similar to that of FIG. 3 but in a rest position with lateral infra-red radiators swung into the centre.

The lateral arms 5 are each connected to the upper end 4 of the stand tube 3 by means of a joint 19 rotatable about a vertical axis, so that in the rest position the arms 5 with the lateral radiators 6 are tilted towards one another into the centre, as illustrated in FIG. 4, thus reducing the space occupied by the heat treatment apparatus when not in use.

Figure 5:
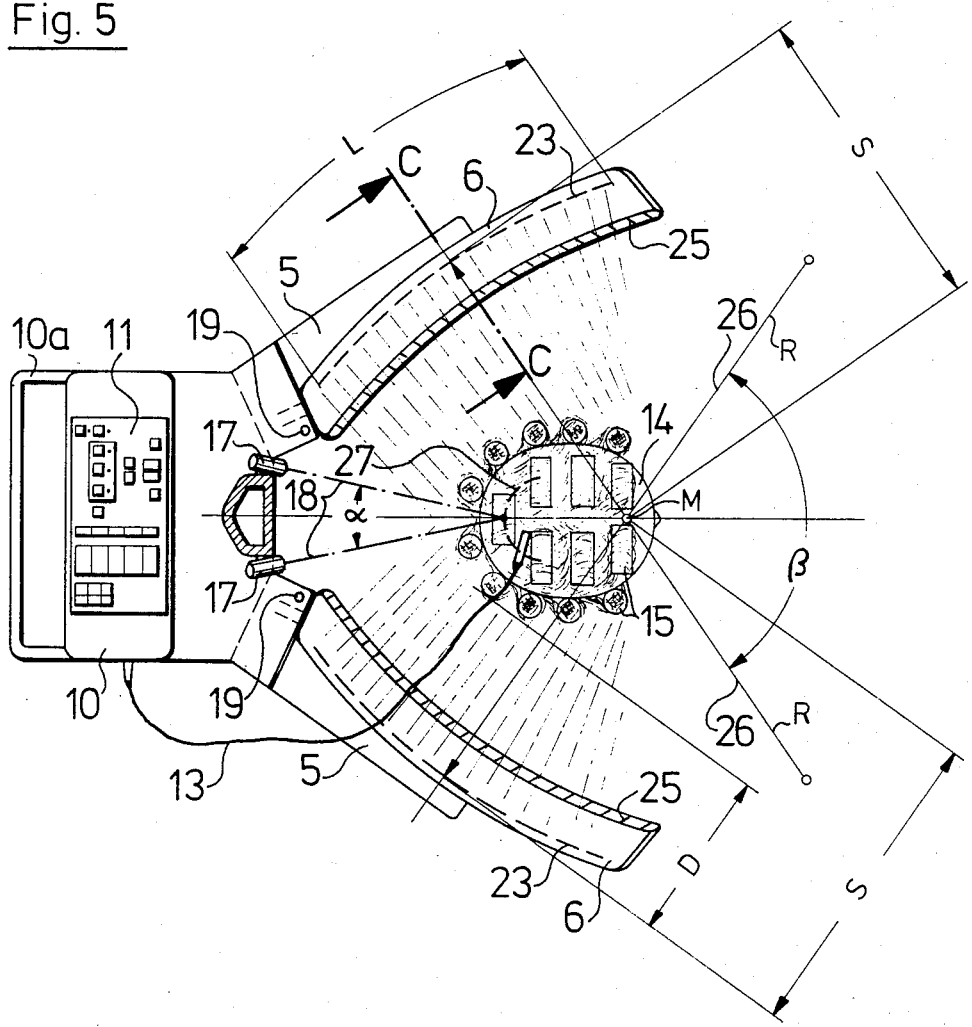
FIG. 5 is a horizontal section on the line A—A in FIG. 1 in the first position of use (in conjunction with a head to be treated)

The construction of the infra-red radiators 6,9 may best be seen from FIGS. 3 and 5. Each radiator 6 or 9 comprises an elongate slightly curved tubular heating element 23 of quartz glass which is arranged in front of a reflector 24. The open side of each radiator 6,9 is covered by a grid 25 operating as a protection against contact.

FIG. 5 clarifies the longitudinal curvature of the heating element 23, which preferably has a radius of curvature R of 800 mm. The median axis 26 of each of the two lateral radiators 6 defines the respective main radiation direction. The median axes 26 of the two lateral radiators 6 preferably include between them an angle $\beta$ of 108°, the spacing S of the common intersection point M from the respective heating element 23 amounting to approximately half the radius of curvature R.

The ratio between the length L of each heating element 23 and its respective radius of curvature R amounts to at least 0.4, preferably 0.6. It has been found that it is advantageous if the received power of an infra-red radiator amounts to 250 W, and the minimum distance D between each heating element 23 and the hair or—when curl rollers are used—each curl roller preferably amounts to 25 to 30% of the prevailing radius of curvature R. The longitudinal axis of each lateral radiator 6 has a rise angle $\phi$ of approximately 10° to 12° relatively to the horizontal 29, as indicated in FIG. 1.

FIG. 5 shows the optical beam axes 18 of the projector lamps 17, the common intersection point of which lies in the region of the hair line on the neck contour 27 indicated in broken line.

Figure 6:
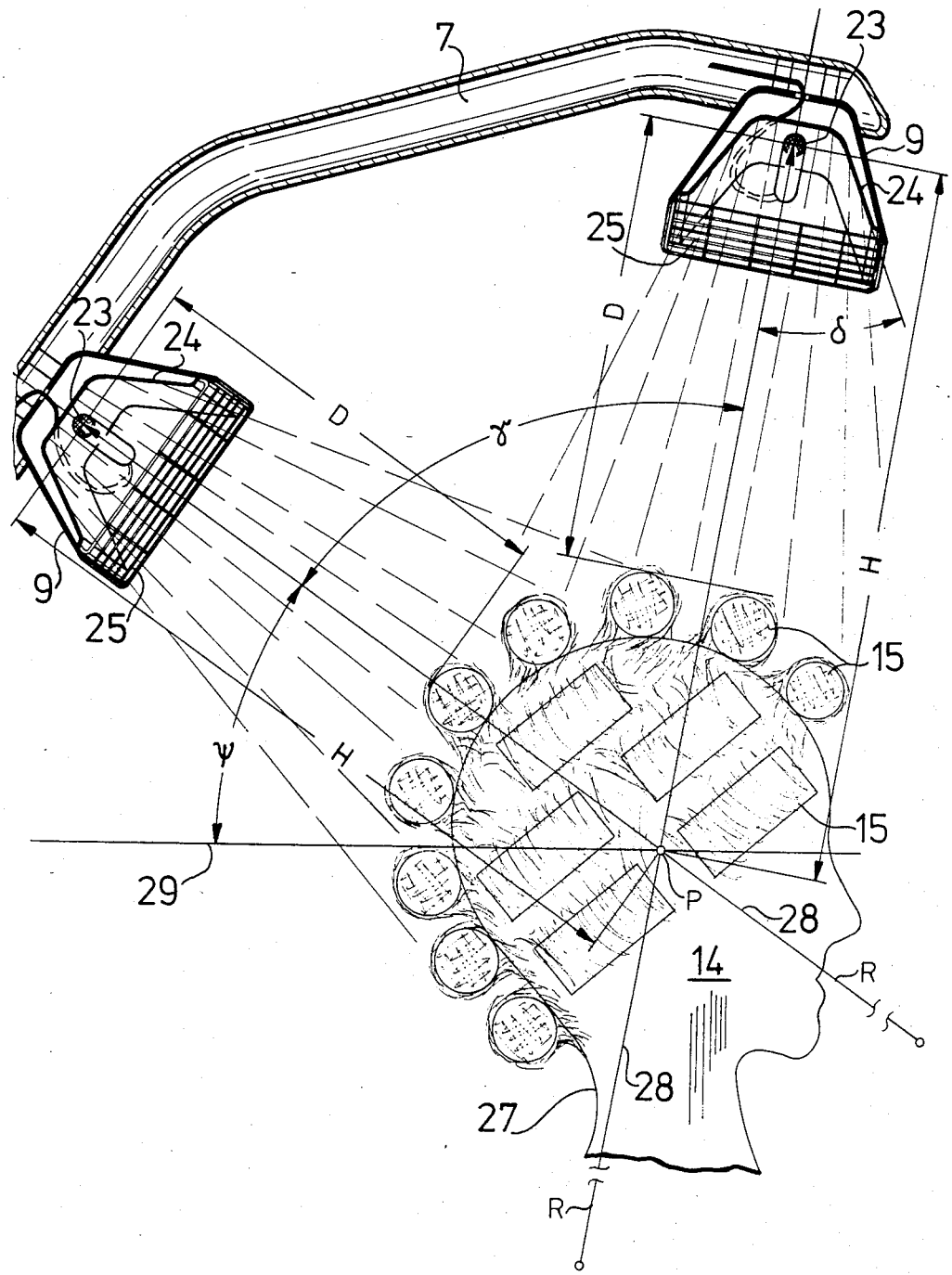
FIG. 6 is a vertical section on the line B—B in FIG. 3 through the central infra-red radiators on the enlarged scale (in conjunction with a head to be treated)

The geometry of the central infra-red radiators 9 illustrated in FIG. 6 is analogous to the arrangement illustrated in FIG. 5 of the lateral infra-red radiators 6. The median axes 28 of the two central radiators 9 preferably include between them an angle $\gamma$ of 68.5°, the distance H of the common intersection point P from the respective tubular heating element 23 preferably amounting to approximately half the radius of curvature R. Furthermore, the median axis 28 of the lower one of the central radiators 9 and the horizontal 29 include between them an angle $\psi$ of approximately 55°. It is attained thereby that a comfortable head position can be assumed in the sitting position.

Figure 7:
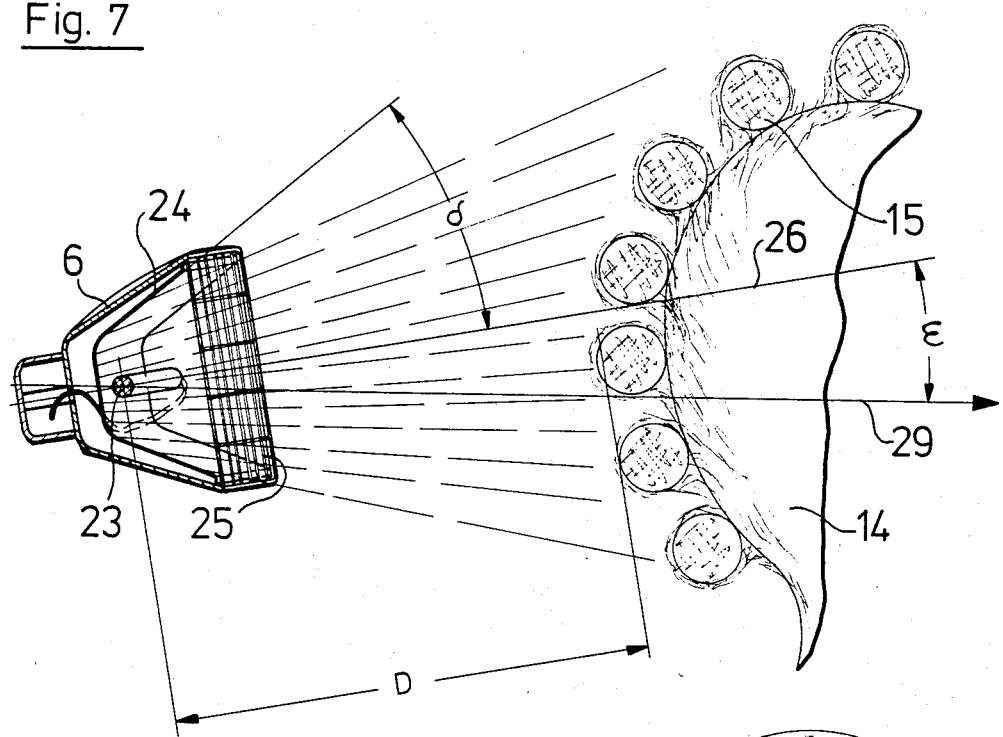
FIG. 7 is a vertical section on the line C—C in FIG. 5 through a lateral infra-red radiator, on the enlarged scale, in the first position of use (in conjunction with a head to be treated)
Figure 8:
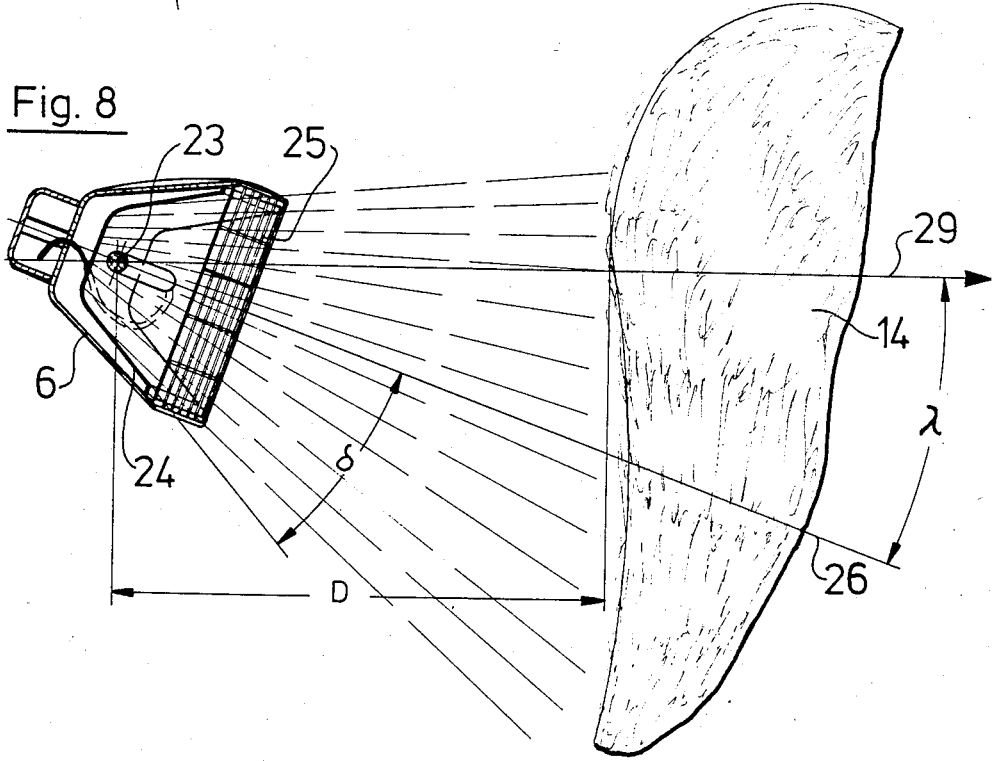
FIG. 8 is a vertical section similar to FIG. 7 but in a second position of use, in which the lateral infra-red radiator is swung to a lower tilt position for long hair.

The minimum spacing D of each heating element 23 from the hair or—when curl rollers are used—from the respective curl roller preferably amounts to 25 to 30% of the prevailing radius of curvature R. The reflector 24 in each central radiator 9 is in the form of a channel section with divergent side walls, i.e. in cross-section it is shaped as a trapezium, with limbs preferably of equal lengths, the base being perpendicular to the optical beam axis 18. It is attained thereby that the radiation is not focussed along a line on the head, but as uniform an irradiation as possible of the surface of the head is obtained. As may be seen more clearly from FIG. 7, the semi-opening angle $\delta$ of the reflector 24 is approximately 30°. In relation to the horizontal 29, the median axis 26 of each of the lateral radiators 6 is inclined upwardly, preferably by an angle $\epsilon$ of 10°, to a first position of use for hair preferably wound upon curl rollers, or short hair. For the treatment of long hair, in particular hair of shoulder length, the lateral radiators 6 may be swung downwards into a second position of use, as illustrated in FIG. 8. In this case the median axis 26 is inclined downwardly by an angle $\lambda$ (preferably 20°) relatively to the horizontal 29. Thus the swing range $(\epsilon + \lambda)$ of the lateral radiators 6 preferably amounts to 30°.

Three different hair treatment processes are possible by means of the above-described apparatus, namely a permanent waving programme, a remedial and dyeing programme, and a drying programme, each of which will be described below.

(a) Permanent waving programme

Figure 10:
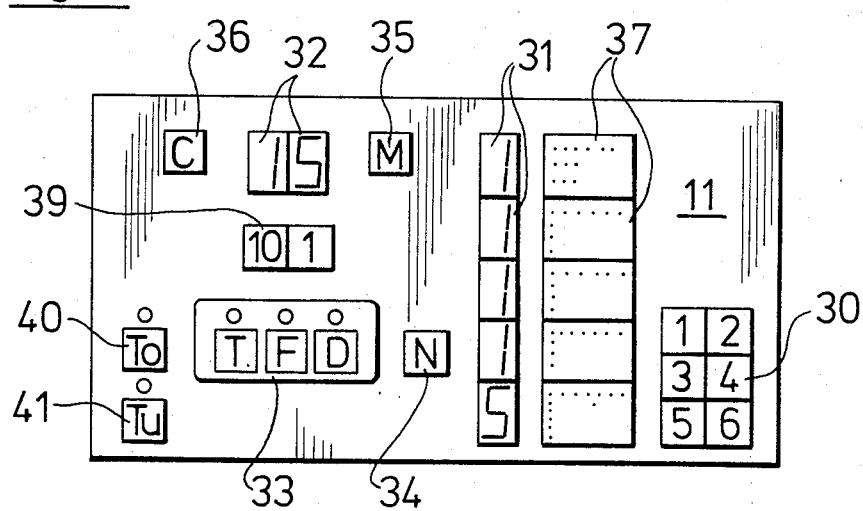
FIG. 10 is an enlarged view of the operating panel of the control desk illustrated in FIG. 2 and FIG. 5.

The control panel 11 illustrated in FIG. 10 comprises at the bottom right six press keys of a first key field 30 for inserting the numbers 1 to 6, each key always being allocated to a separate number value and provided on its operating side with the corresponding numer value inscription. Five different number values can be inserted successively by depressing the respective key, the respective successively inserted number values being indicated on below another from top to bottom in five single-position 7-segment indicators (LED) 31, in an appropriately associated arrangement. For example, in FIG. 10 the number values 1-1-1-1-5 have been successively inserted in the control panel 11 and are correspondingly indicated on the indicators 31. When a non-permissible number value is inserted, the corresponding indicator 31 blinks and the permanent waving programme selected is blocked. The number value adjusted in the lowest indicator 31 (provided with the number "5" in FIG. 10) is a code number for the kind of permanent waving treatment previously performed on the hair. The dwell period stored for this in the internal programme store is subsequently indicated by a two-position 7-segment indicator 32 (for example, a dwell period of 15 min is indicated in FIG. 10). After depression of the key denoted by "D" of a second key field 33, the permanent waving programme is started. The dwell period still remaining is indicated by the indicator 32 (e.g. the dwell period of 15 min given by way of example would be reduced in steps of one minute by means of a backward counter). The permanent waving programme switches off when the dwell period still remaining is indicated as zero. During the running period of this permanent waving programme, the lateral and central infra-red radiators 6 and 9 heat the hair, the temperature sensor 12 (secured by a curl roller 15) measuring the temperature produced and the heating power of the heating elements 23 being controlled accordingly by an internal control, preferably by switching off and on. A nominal temperature in the range of 45° C. to 55° C., preferably 50° C., is adjusted at the temperature sensor 12.

After the termination of the permanent waving programme, an additional dwell period predetermined by the programme can be selected by depressing the key 34 denoted by "N" and is indicated by the indicator 32. By repeated depression of the key denoted by "D" of the second key field 33 the associated backward counter is started and the remaining additional dwell period is appropriately counter backwards down to zero. This process may be repeated several times, until the permanent waving treatment is concluded. In order that the user may recognise the end of the respective heating period in good time, at a remaining running speed of 3 min indicated by the indicator 32 the number starts to blink, and from a remaining running period of 10 sec onwards additionally an acoustic buzzer is started. For the purpose of monitoring the originally predetermined dwell period or additional dwell period, the number value thereof can be indicated briefly on the indicator 32 by depressing for a short time the key 35 denoted by "M". Furthermore, the control panel 11 is provided with a key 36 denoted by "C", upon depression of which the prevailing permanent waving programme is stopped and the cancellable store contents are cancelled and thus also the heating by means of the infra-red radiators 6,9 is switched off. For example, in the case of insertion of a wrong number value by means of a key of the first key field 30 all single-position 7-segment indicators 31 can be cancelled by depressing the key 36 denoted by "C" and thereafter correctly inserted again. The respective associated pre-selectable number values for the permanent waving programme are arranged on inscribed fields 37 (not illustrated in detail) which are disposed adjacent the respective single-position 7-segment indicators 31.

(b) Remedial and dyeing programme

In this case the effect on the hair during hair dyeing or upon deposition of care emulsion is to be improved, in particular accelerated, by the influence of heat. For this purpose, by means of a third key field 39, the dwell period is adjusted by depressing its tens and units keys (the corresponding denominations "10" and "1" are provided on the keys 39 in FIG. 10) and is indicated by the indicator 32. AS long as the corresponding key remains depressed, the respective tens or units position, respectively, of the number value of the dwell period is counted up at a slow rhythm. Upon depression of a key denoted by "F" of the second key field 33, the remedial and dyeing programme is started; it is switched off owing to expiry of time when a remaining dwell period of zero is attained. In this case the nominal temperature at the hair sensor 12 is preferably 40° C., which is preferably produced at a heating power of 250 W per infra-red radiator 6,9 by means of an impulse pause ratio between a switch-on period of 13 sec and a switch-off period of 8 sec. The indication of the end of this programme is effected analogously to the permanent waving programme.

(c) Drying programme

The heat treatment apparatus may likewise be used for drying wet hair. The dwell period is inserted correspondingly by means of the third key field 39 and is started by means of a key denoted by "T" of the second key field 33. According to an internally stored programme the infra-red radiators are initially operated at maximum heating power, preferably for 5 min. Thereafter the heating power is appropriately reduced by means of an impulse pause ratio between approximately 15 sec switch-on period and 7 sec switch-off period. Such an impulse pause control is effected in a known manner by means of so-called triac semiconductors. The treated person may switch over to a reduced heating power having an impulse pause ratio of preferably 10 sec switch-on duration to 9 sec switch-off duration by means of a switch (not illustrated) which is arranged on the front of the upper central infra-red radiator; the temperature of the hair is reduced thereby in a corresponding manner. The lateral radiators 6 may be switched off by means of a key 40 denoted by "To", so that solely the central infra-red radiators 9 are heated. Alternatively, by depressing the key 41 denoted by "Tu" the central radiators 9 may be switched off, so that solely the lateral heaters 6 are heated. This switching on and off can be performed in all three programmes and permits individual adjustment to the hair-do of the person to be treated.

MODE OF OPERATION

A person whose hair is to be treated sits, for example, on an appropriate chair arranged within the irradiation range of the infra-red radiators and assume a position similar to that illustrated in FIG. 1. The required minimum spacing D is then adjusted by means of the projector lamps 17 in such a manner that the horizontal line 20 and the vertical line 21 together form an equal limbed cross 22 in the region of the neck contour 27 of the hair line in accordance with FIG. 9. For example, the hair strands have already be wound upon curl rollers and appropriately wetted with permanent waving fluid.

For accelerating the conversion process in the keratin of the hair, the previously described permanent waving programme is then started. If, because of the particular hair construction, for example thick hair, the dwell period predetermined by the permanent waving programme is not sufficient, this dwell period is appropriately lengthened by a predetermined value by means of actuation of the key 34 denoted by "N" (FIG. 10). The operator of the heat treatment apparatus is rendered aware of the end of the heat treatment by an optical and towards the end also an acoustic warning signal. Selectively, one of the other two programmes may be started correspondingly in the manner described above.

FIG. 11 illustrates a second embodiment of the heat treatment apparatus in which, instead of a stand, a wall bracket 42 supports the support arm 7. In a known manner the bracket 42 consists of a socket 43 secured to the wall and carrying an upper arm 45 which is rotatable about a vertical axis 44 and at the other end of which a lower arm 49 is arranged which is selectively rotatable about a vertical axis 46 and vertically pivotable about a horizontal axis 47. At the other end of the lower arm 49 a projection 51 is articulated about a horizontal axis 50 by way of a parallel motion guide and supports the selectively horizontally rotatable support arm 7. Thereby the infra-red radiators 6 and 9 may be adjusted in a known manner by means of the hand grip 10a to any desired position relatively to the head 14 to be treated, at a predetermined minimum spacing D.

In a further embodiment (not shown), in place of the optical adjusting device carrying two projector lamps 17, another spacing device e.g. of a mechanical kind, may be used for adjusting the minimum spacing of the head 14 from the infra-red radiators 6 and 9.

We claim:

1. Heat treatment apparatus for heating human hair on the head, comprising a support (7), two lateral infra-red radiators (6) mounted on the support (7) and extended from said support inwardly of the apparatus so as to embrace the human head at two sides thereof, and at least one central infra-red radiator (9) mounted above the lateral radiators (6) on the support (7), each radiator (6, 9) comprising an arcuate linear heating element (23), the ratio between the length (L) of the heating element (23) and its radius of curvature (R) being at least 0.2, each radiator having a radial median axis defining the main radiation direction of the radiator, the lateral radiators being mounted on said support such that the radial median axes (26) of the lateral radiators (6) include between them an angle (β) of at least 80°.

2. Apparatus as claimed in claim 1, in which two central infra-red radiators (9) are provided, which are positioned such that their radial median axes (28) include between them an angle (γ) of at least 45°.

3. Apparatus as claimed in claim 2, in which one of the two central intra-red radiators is a lower one on said support and another of the two central intra-red radiators is an upper one, the radial median axis (28) of the lower of the two central radiators (9) making an angle (ψ) of at least 30° with the horizontal (29).

4. Apparatus as claimed in claim 1, in which the radial median axes (26) of the lateral radiators (9) include between them an angle (β) of at least 100°.

5. Apparatus as claimed in claim 1, in which each of said radiators has a longitudinal axis, the longitudinal axis of each of the lateral radiators (6) forming with the horizontal (29) a rise angle (ρ) of at least 5°.

6. Apparatus as claimed in claim 1, in which said lateral radiators are positioned so that the median axes (26) of the lateral radiators (6) are inclined upwardly to the horizontal.

7. Apparatus as claimed in claim 1, in which the lateral radiators (6) are swingable through an angle (ε+λ) of at least 15° from a first position in which their radial median axes (26) are inclined upwardly to the horizontal to a second position in which said axes (26) are inclined downwardly from the horizontal.

8. Apparatus as claimed in claim 1, in which the lateral radiators (6) are swingable about a substantially vertical axis by means of a joint (19) located adjacent the support (7), from the position of use towards one another to a rest position below the at least one central radiator.

9. Apparatus as claimed in claim 1, in which each radiator (6, 9) includes a reflector (24) having a channel-like section with divergent sidewalls.

10. Apparatus as claimed in claim 9, in which the sidewalls include between them an angle (2δ) of 60°.

11. Apparatus as claimed in claim 1, further comprising means for locating an optimum position of the outer contour of the hair in relation to the radiators (6, 9).

12. Apparatus as claimed in claim 11, in which the locating means comprises an optical device.

13. Apparatus as claimed in claim 12, in which the optical device comprises two projector lamps (17) producing intersecting beams which form a sharply reproduced cross (20) on the neck of the person being treated when the outer contour of the hair is in the optimum position.

14. Apparatus as claimed in claim 1, in which each heating element comprises a quartz glass tube (23) and has a radius of curvature (R) of 600 to 1000 mm.

15. Apparatus as claimed in claim 2, in which the radial median axes of the lateral radiators define a common intersection point (M) and the radial median axes of the central radiators define a common intersection point (P), and in which a distance (S or H) from the common intersection point (M or P) of the respective median axes (26 or 28) of the lateral radiators (6) or of the central radiators (9) to the respective heating elements (23) amounts to from 30 to 70% of their mean radius of curvature (R) measured in the main radiation direction.

16. Apparatus as claimed in claim 1, in which the length (L) of the heating element (23) amounts to at least 30% of its radius of curvature (R) measured in the main radiation direction.

17. Apparatus as claimed in claim 1, further comprising a temperature sensor (12) to be arranged in the hair being treated, and a control module which is connected to the temperature sensor (12) and which regulates the heating power of the radiators (6, 9) so as to maintain a predetermined nominal temperature.

18. Apparatus as claimed in claim 17, in which the temperature sensor (12) comprises an NTC resistor embedded in a synthetic resin casing and fixing means are provided on the casing which maintain it in direct contact with hair wound upon a curl roller (15).

19. Apparatus as claimed in claim 1, including a control desk (11) containing electrical control and regulator modules, which controls by means of a microprocessor the heating power of the heating element (23).

20. Apparatus as claimed in claim 19, in which the heating power is controlled by means of triac semi-conductors by way of the impulse pause ratio of the heating current.

21. Apparatus as claimed in claim 1, in which the infra-red radiation produced by the radiators (6, 9) has a wavelength of from 2.3 to 2.7 μm.

22. Apparatus as claimed in claim 1, in which the support comprises a displaceably mounted arm (7) supporting said radiators.

23. Apparatus as claimed in claim 1, in which the length (L) of the heating element (23) amounts to 37 to 57% of its radius of curvature (R) measured in the main radiation direction.

* * * * *